(12) United States Patent
Davidson (10) Patent No.: US 8,369,589 B2
(45) Date of Patent: Feb. 5, 2013

(54) SYSTEM AND METHOD FOR CONCURRENT TRANSFER AND PROCESSING AND REAL TIME VIEWING OF IN-VIVO IMAGES

(75) Inventor: Tal Davidson, Yoqneam Illit (IL)

(73) Assignee: Given Imaging Ltd., Yoqneam (IL)

( * ) Notice: Subject to any disclaimer, the term of this patent is extended or adjusted under 35 U.S.C. 154(b) by 1373 days.

(21) Appl. No.: 12/065,635

(22) PCT Filed: Sep. 10, 2006

(86) PCT No.: PCT/IL2006/001054
§ 371 (c)(1),
(2), (4) Date: Mar. 4, 2008

(87) PCT Pub. No.: WO2007/029261
PCT Pub. Date: Mar. 15, 2007

(65) Prior Publication Data
US 2008/0260223 A1    Oct. 23, 2008

Related U.S. Application Data (60) Provisional application No. 60/715,158, filed on Sep. 9, 2005.

(51) Int. Cl.
*G06K 9/54* (2006.01)
*A61B 1/045* (2006.01)
(52) U.S. Cl. .............. 382/128; 348/77; 600/476
(58) Field of Classification Search .......... 382/128–133; 600/371, 476
See application file for complete search history.

(56) References Cited

U.S. PATENT DOCUMENTS

| | | |
|---|---|---|
| 4,278,077 A | 7/1981 | Mizumoto |
| 5,604,531 A | 2/1997 | Iddan et al. |
| 5,993,378 A | 11/1999 | Lemelson |
| 6,240,312 B1 | 5/2001 | Alfano et al. |
| 6,771,262 B2 | 8/2004 | Krishnan |
| 7,914,442 B1 * | 3/2011 | Gazdzinski .............. 600/109 |
| 2001/0031920 A1 * | 10/2001 | Kaufman et al. ........... 600/431 |
| 2002/0103417 A1 | 8/2002 | Gazdzinski |
| 2003/0151661 A1 | 8/2003 | Davidson et al. |
| 2005/0048456 A1 * | 3/2005 | Chefd'hotel et al. ........ 434/267 |
| 2005/0074151 A1 | 4/2005 | Chen et al. |

(Continued)

FOREIGN PATENT DOCUMENTS

| | | |
|---|---|---|
| DE | 344 0177 | 5/1986 |
| EP | 0 677 272 | 10/1995 |

(Continued)

OTHER PUBLICATIONS

Oh et al. "Binary Frame Detection and Shot Segmentation in Colonoscopy Videos", Storage and Retrieval Methods and Applications for Multimedia, 2004, p. 531-542.*

(Continued)

*Primary Examiner* — Robert Kim
*Assistant Examiner* — David E Smith
(74) *Attorney, Agent, or Firm* — Pearl Cohen Zedek Latzer, LLP (57) ABSTRACT

Embodiments of the present invention provide a system and method for a concurrent transferring of an image stream gathered by an in-vivo sensing device, including creating a plurality of segments from at least a portion of the image stream and concurrently transferring the created segments. Other embodiments of the present invention provide and system and method for a concurrent processing of an image stream gathered by an in-vivo sensing device, including creating a plurality of segments from at least a portion of the image stream and concurrently processing the created segments.

22 Claims, 4 Drawing Sheets

U.S. PATENT DOCUMENTS

| | | | |
|---|---|---|---|
| 2005/0075537 A1* | 4/2005 | Chen et al. | 600/109 |
| 2006/0165169 A1* | 7/2006 | Ng et al. | 375/240.12 |
| 2007/0053557 A1* | 3/2007 | Cahill et al. | 382/128 |
| 2007/0071297 A1 | 3/2007 | Geiger et al. | |

FOREIGN PATENT DOCUMENTS

| | | |
|---|---|---|
| EP | 1765144 | 1/2006 |
| JP | 57-45833 | 3/1982 |
| JP | 4-109927 | 4/1992 |
| JP | 1992-144533 | 5/1992 |
| WO | WO 01/65995 | 9/2001 |
| WO | WO 02/073507 | 9/2002 |
| WO | WO 03/069913 | 8/2003 |
| WO | WO 2006/003650 | 1/2006 |

OTHER PUBLICATIONS

Bhandarkar and Chandrasekaran, "Parallel Parsing of MPEG Video on a Shared-Memory Symmetric Multiprocessor," Parallel Computing 30, 2004, p. 1233-1276.*

Oh, et al. "Binary Frame Detection and Shot Segmentation in Colonoscopy Videos", Storage and Retrieval Methods and Applications for Multimedia, 2004, p. 531-542.*

Bhandarkar and Chandrasekaran, "Parallel Parsing of MPEG Video on a Shared-Memory Symmetric Multiprocessor", Parallel Computing 30, 2004, p. 1233-1276.*

International Search Report for International Application No. PCT/IL06/01054 mailed Aug. 15, 2007.

Oh J H, et al. "Blurry Frame Detection and Shot Segmentation in Colonoscopy Videos" Proc SPIE, vol. 5307, pp. 531-542 Jan. 22, 2004 to Jan. 24, 204.

Bhandarkar S M, et al. "Parallel Parsing of MPEG Video on a Shared-Memory Symmetric Multiprocessor" Parallel Computing, Elsevier Publishers Amsterdam NL, vol. 30, No. 11, pp. 1233-1276, Nov. 1, 2004.

Butz T, et al. "Shot Boundary Detection With Mutual Information", Proc. 2001 International Conference on Image Processing, Thessaloniki, Greece, vol. 3, pp. 422-425, Oct. 7, 2001.

International Preliminary Report on Patentability of Application No. PCT/IL2006/001054 issued on Mar. 11, 2008.

* cited by examiner

SYSTEM AND METHOD FOR CONCURRENT TRANSFER AND PROCESSING AND REAL TIME VIEWING OF IN-VIVO IMAGES

CROSS-REFERENCE TO RELATED APPLICATIONS

This application is a National Phase Application of PCT International Application No. PCT/IL2006/001054, entitled "SYSTEM AND METHOD FOR CONCURRENT TRANSFER AND PROCESSING AND REAL TIME VIEWING OF IN-VIVO IMAGES", International Filing Date Sep. 10, 2006, published on Mar. 15, 2007 as International Publication No. WO 2007/029261, which in turn claims priority from US Provisional Patent Application No. 60/715,158, filed Sep. 9, 2005, both of which are incorporated herein by reference in their entirety.

FIELD OF THE INVENTION

The present invention relates to in vivo imaging. More specifically the invention relates to an apparatus and method for concurrent transfer and processing of information gathered by an in-vivo sensing device.

BACKGROUND OF THE INVENTION

In-vivo devices, such as, for example, capsules having image capturing capabilities, may transmit streams of images while progressing through body lumens. Such a stream of images may be recorded in a memory of a recording device and may be used by human operators as, for example, a source of information regarding the health condition of such body lumens. Such captured image information may be processed (e.g., feature detection, color correction, etc.) after or during transfer from a recording device to for example a workstation; this may take more time than desired.

SUMMARY

Embodiments of the present invention provide a system and method for a concurrent transferring of an image stream gathered by an in-vivo sensing device, including creating a plurality of segments from at least a portion of the image stream and concurrently transferring the created segments. Other embodiments of the present invention provide and system and method for a concurrent processing of an image stream gathered by an in-vivo sensing device, including creating a plurality of segments from at least a portion of the image stream and concurrently processing the created segments.

BRIEF DESCRIPTION OF THE DRAWINGS

Embodiments of the invention are illustrated by way of example and not limitation in the figures of the accompanying drawings, in which like reference numerals indicate corresponding, analogous or similar elements, and in which.

It will be appreciated that for simplicity and clarity of illustration, elements shown in the figures have not necessarily been drawn to scale. For example, the dimensions of some of the elements may be exaggerated relative to other elements for clarity.

DETAILED DESCRIPTION OF THE INVENTION

In the following detailed description, numerous specific details are set forth in order to provide a thorough understanding of embodiments of the invention. However it will be understood by those of ordinary skill in the art that the embodiments of the invention may be practiced without these specific details. In other instances, well-known methods, procedures, components and circuits have not been described in detail so as not to obscure the embodiments of the invention.

According to some embodiments of the present invention, an in-vivo sensing system may include an in-vivo sensing device, such as, for example, a capsule having image capturing capabilities, a receiver/recorder, to receive a stream of images from the in-vivo sensing device and to store the stream of images in a memory for a later use, and a workstation which receives images and other data from the receiver/recorder. In vivo sensing systems other than capsules may be used.

Figure 1:
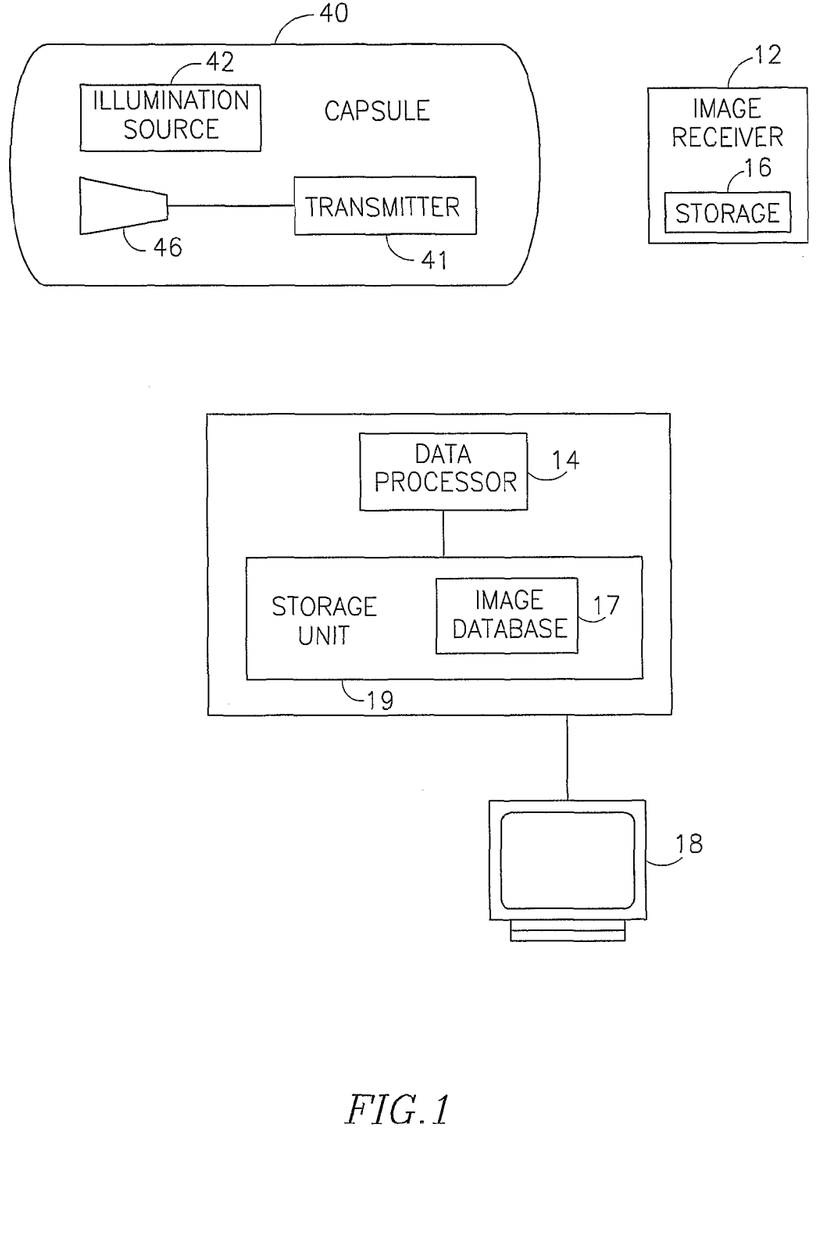
FIG. 1 is a schematic diagram of an in vivo imaging system according to one embodiment of the present invention.

Reference is made to FIG. 1, which shows a schematic diagram of an in vivo imaging system according to one embodiment of the present invention. In an exemplary embodiment, the system comprises an in-vivo device 40 such as a capsule having an imager 46, for capturing images, an illumination source 42, for illuminating the body lumen, and a transmitter 41, for transmitting image and possibly other information to a receiving device. An optical system (not shown), including, for example, lenses or mirrors, may aid in focusing reflected light onto the imager 46. The device 40 is swallowed by a patient and preferably traverses the patient's GI tract. In certain embodiments, the in-vivo imaging device and image capture system are similar to embodiments described in U.S. Pat. No. 5,604,531 or in WO 01/65995, both assigned to the common assignee of the present application and incorporated herein by reference in their entirety. In one embodiment, a receiver/recorder, or methods of accessing a receiver/recorder, and also an in-vivo imaging device and viewing system, may be similar to embodiments described in International Application PCT/IL2005/000696, filed Jun. 30, 2005, and entitled "In Vivo Sensing System Device And Method For Real Time Viewing", assigned to the common assignee of the present application and incorporated herein by reference in its entirety. In alternate embodiments, other capsules or other image capture devices, and other image capture systems, having other configurations, may be used.

Preferably, located outside the patient's body in one or more locations, are an image receiver 12, preferably including an antenna or antenna array, an image receiver storage unit 16, a data processor 14, a data processor storage unit 19, and an image display 18, for displaying, inter alia, the images recorded by the device 40 and annotation information. Preferably, the image receiver 12 and image receiver storage unit 16 are small and portable, and are worn on the patient's body during recording of the images. Data processor storage unit 19 includes an image database 17. Preferably, data processor 14, data processor storage unit 19 and display 18 (e.g., a monitor) are part of a personal computer or workstation which includes standard components such as processor 14, a memory, a disk drive, and input-output devices, although alternate configurations are possible, and the system and method of the present invention may be implemented on various suitable computing systems.

Data processor 14 may include any standard data processor, such as a microprocessor, multiprocessor, accelerator board, or any other serial or parallel high performance data processor for concurrently processing a plurality of images. Image display 18 may be a computer screen, a conventional video display, or any other device capable of providing image or other data.

Preferably, the imager 46 is a suitable CMOS camera, such as a "camera on a chip" type CMOS imager. In alternate embodiments, the imager 46 may be another device, for example, a CCD. The illumination source 42 may be, for example, one or more light emitting diodes, or another suitable light source.

In operation, imager 46 captures images and sends data representing the images to transmitter 41, which transmits images to image receiver 12 using, for example, electromagnetic radio waves. Image receiver 12 transfers the image data to image receiver storage unit 16. After a certain period of time of data collection, the image data stored in storage unit 16 is sent to the data processor 14 or the data processor storage unit 19. For example, the image receiver storage unit 16 may be taken off the patient's body and connected to the personal computer or workstation which includes the data processor 14 and data processor storage unit 19 via a standard data link, e.g., a serial or parallel interface of known construction. The image data is then transferred from the image receiver storage unit 16 to the image database 17 within data processor storage unit 19. Data processor 14 may analyze the data and provide the analyzed data to the image display 18, where a health professional views the image data. Data processor 14 operates software (not shown) which, in conjunction with basic operating software such as an operating system and device drivers, controls the operation of data processor 14. Preferably, the software controlling data processor 14 includes code written in the C++ language and possibly additional languages, but may be implemented in a variety of known methods.

The image data collected and stored may be stored indefinitely, transferred to other locations, or manipulated or analyzed. A health professional may use the images to diagnose pathological conditions of the GI tract, and, in addition, the system may provide information about the location of these pathologies. In some embodiments the image data is not viewed in real time, but some embodiments allow for real time viewing or for viewing of data very soon after collection, while image data is still being collected.

The image display 18 presents the image data, preferably in the form of still and moving pictures, and in addition may present other information. Preferably, the in vivo imager system collects a series of still images as it traverses the GI tract. The images may be later presented as, for example, a stream of images or a moving image of the traverse of the GI tract. The in vivo imager system may collect a large volume of data, as the device 40 may take several hours to traverse the GI tract, and may record images at a rate of, for example, two images every second, resulting in the recordation of thousands of images, for example 50,000 images. The image recordation rate (or frame capture rate) may be varied.

Preferably, the image data recorded and transmitted by the device 40 is digital color image data, although in alternate embodiments other image formats may be used. In an exemplary embodiment, each frame of image data includes 256 rows of 256 pixels each, each pixel including bytes for color and brightness, according to known methods. For example, in each pixel, color may be represented by a mosaic of four sub-pixels, each sub-pixel corresponding to primaries such as red, green, or blue (where one primary is represented twice). The brightness of the overall pixel may be recorded by a one byte (i.e., 0-255) brightness value. Preferably, images are stored sequentially in data processor storage unit 19. The stored data may be comprised of one or more pixel properties, including color and brightness.

While, preferably, information gathering, storage and processing are performed by certain units, the system and method of the present invention may be practiced with alternate configurations. For example, the components gathering image information need not be contained in a capsule, but may be contained in any other vehicle suitable for traversing a lumen in a human body, such as an endoscope, stent, catheter, needle etc.

Preferably, data processor storage unit 19 stores a series of images recorded by device 40. The images the device 40 records as it moves through a patient's GI tract may be combined or attached, for example, consecutively, to form an image stream or moving images. This image stream may be displayed in a window on display 18. The image stream may be frozen to view one frame, speeded up, or reversed; sections may be skipped; or any other method for viewing an image may be applied to the image stream. While the following discussion relates to the case where data from device 40 is stored for later use, the system and method of the present invention may be used alternatively with systems allowing for real time viewing of image data or for the viewing of data while other data is being collected.

In an exemplary embodiment, the image stream is stored as a series of images in the image database 17, which may be implemented in a variety of known manners.

Figure 2:
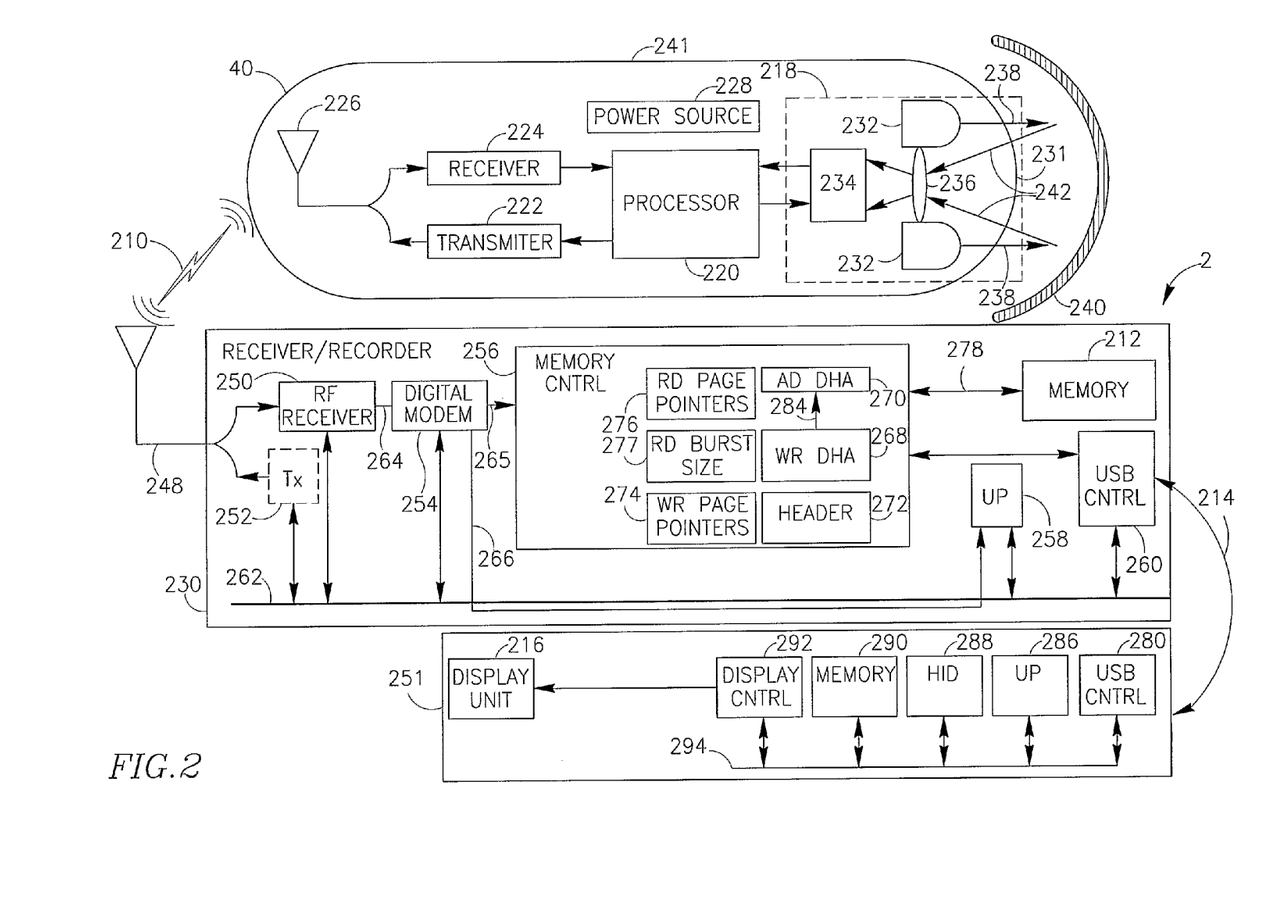
FIG. 2 is a block-diagram illustration of the in-vivo sensing system, in accordance with some embodiments of the present invention.

FIG. 2 is a block-diagram illustration of an in-vivo sensing system 2, in accordance with some embodiments of the present invention. According to some embodiments of the present invention the in-vivo sensing system 2 may include an in-vivo sensing device 40, a receiver/recorder 230 (which may be similar to recorder 12, FIG. 1) and a device 251, which may be included in a workstation. Components of FIG. 2 may be similar to those described in FIG. 1 or other embodiments herein. For example, device 251 may include the data processor 14 and image display 18.

According to some embodiments of the present invention, in-vivo sensing device 40 may include a container or housing 241. Within the housing 241, may be, for example, an imaging system 218, a processor 220 (e.g., a control block), a transmitter 222, a receiver 224 and an antenna 226. According to one embodiment of the present invention, sensing device 40 may include a power source 228 to provide power to at least imaging system 218, processor 220, transmitter 222, and optional receiver 224.

According to one embodiment of the present invention, all of the components may be sealed within the sensing device 40 body (the body or shell may include more than one piece); for example, an imaging system, power source, and transmitting and control systems, may all be sealed within the sensing device 40 body.

According to some embodiments of the present invention, sensing device 40 typically may be or may include an autonomous swallowable capsule, but device 40 may have other shapes and need not be swallowable or autonomous. Embodiments of device 40 are typically autonomous, and are typically self-contained. For example, device 40 may be a capsule or other unit where all the components are substantially contained within a container or shell, and where device 40 does not require any wires or cables to, for example, receive power or transmit information.

Transmitter 222 may include control capability for, for example controlling the various operations of device 40, although control capability or one or more aspects of control may be included in a separate component.

Power source 228 may include batteries, such as, for example, silver oxide batteries, Lithium batteries, capacitors, or any other suitable power source. In another embodiment of the present invention, power source 228 may not be present and the device may be powered by an external power source, for example, by a magnetic field or electric field that transmits to the device.

Imaging system 218 may include an optical window 231, at least one illumination source 232, such as, for example, a light emitting diode (LED), an OLED (Organic LED) an imaging sensor 234, and an optical system 236, which may include for example one or more lens. Other suitable illumination sources may be used.

Imaging sensor 234 may include a solid state imaging sensor, a complementary metal oxide semiconductor (CMOS) imaging sensor, a charge coupled device (CCD) imaging sensor, a linear imaging sensor, a line imaging sensor, a full frame imaging sensor, a "camera on chip" imaging sensor, or any other suitable imaging sensor.

Processor 220 may control, at least in part, the operation of sensing device 40. Processor 220, transmitter 222, receiver 224 and imaging sensor 234 may be implemented on any combination of semiconductor dies. For example, and although the invention is not limited in this respect, processor 220, transmitter 222 and receiver 224 may be parts of a first semiconductor die, and imaging sensor 234 may be a part of a second semiconductor die. Moreover, such a semiconductor die may be an application-specific integrated circuit (ASIC) or may be part of an application-specific standard product (ASSP).

Reflections 242 of light rays 238 from inner portion 240 of a body lumen (e.g., the GI tract, a blood vessel, a reproductive lumen, etc.) may penetrate optical window 231 back into sensing device 40 and may be focused by optical system 236 onto imaging sensor 234. Transmitter 222 may transmit the image through antenna 226 into wireless medium 210. A stream of images of inner portions of the body lumen may be transmitted from sensing device 40 through wireless medium 210.

Device 40 may transmit captured images embedded in "wireless communication frames". A payload portion of a wireless communication frame may include a captured image and may include additional data, such as, for example, telemetry information and/or cyclic redundancy code (CRC) and/or error correction code (ECC). In addition, a wireless communication frame may include an overhead portion that may contain, for example, framing bits, synchronization bits, preamble bits, and the like.

According to some embodiments of the present invention, the receiver/recorder 230 may include for example an antenna 248, a receiver, such as, for example, RF receiver 250, an optional transmitter (TX) 252, a digital modem 254, a memory controller 256, a processor (uP) 258, and a communication controller, such as, for example, a universal serial bus (USB) controller 260. According to other embodiments of the invention, transmitter 52 may be a unit separate from receiver/recorder 230.

Receiver/recorder 230 or 12 may be for example portable and worn on a patient during data collection, and later attached to for example data processor 14 or device 251. If simultaneous or early viewing is desired, connection to a data processor or workstation may be done earlier.

According to some embodiments of the present invention, processor 258 may be able to control the operation of RF receiver 250, optional transmitter 252, digital modem 254, memory controller 256, and USB controller 260 through, for example, a bus 262. In addition, RF receiver 250, optional transmitter 252, digital modem 254, memory controller 256, processor 258 and USB controller 260 may be able to exchange data, such as, for example, images received from sensing device 40, or portions thereof, over bus 262. It may be appreciated, that other methods for control and data exchange are possible, and are under the scope of the invention.

Antenna 248 may be mounted inside or outside receiver/recorder 230, and both RF receiver 250 and optional transmitter 252 may be coupled to antenna 248. According to some embodiments of the present invention, the transmitter 252 may be able to transmit wireless messages to sensing device 40 through antenna 248. RF receiver 250 may be able to receive transmissions, such as, for example, a stream of wireless communication frames, from sensing device 40 through antenna 248, and may output signal 264, corresponding to the received wireless communication frames.

The digital modem 254 may receive the sampled analog signal bits 264 of RF receiver 250, and may output digital bits 265 that are made from the analog signal 264, and may for example output a payload valid indication 266, that is received by processor 258. According to some embodiments of the present invention, payload valid indication 266 may be asserted by digital modem 254 to, for example, a high logic level, during payload portion, and may be de-asserted by digital modem 254 to, for example, a low logic level, otherwise. Payload bits 265 may be received by memory controller 256 and payload valid indication 266 may be received by processor 258.

The memory controller 256 may include a write direct memory access (DMA) controller 268, a read DMA controller 270, a header storage 272, a write page pointers storage 274, a read page pointers storage 276 and a read/write burst size storage 277. In response to assertion of payload valid indication 266, processor 258 may store in write page pointers storage 274 pointers to pages in memory 212, and may optionally store a header in header storage 272. In addition, processor 258 may activate write DMA controller 268 to receive payload bits 265 of a wireless communication frame from digital modem 254, and to store the payload bits 265 in memory 212. According to some embodiments of the present invention, the receiver/recorder 230 may communicate with device 251 and/or a portable device via medium 214. For example, according to some embodiments of the present invention, receiver/recorder 230 may be able to transfer payloads recorded on memory 212 to device 251, and may be able to receive controls from device 251. Although the invention is not limited in this respect, medium 214 may be, for example, a USB cable and may be coupled to USB controller 260 of receiver/recorder 230 and to a USB controller 280 of device 251. Wired communications methods, parallel or serial, other than USB, may be used. Alternatively, medium 214 may be wireless, and receiver/recorder 230 and device 251 may communicate wirelessly.

The receiver/recorder 230 may receive from device 251 via USB controller 260 or another suitable link a control to, for example, start sending a stream of payloads as received from sensing device 40 to device 251, starting at a particular payload of the stream. USB controller 260 may forward the control to processor 258 via bus 262.

According to some embodiments of the present invention, in response to the control received from device 251, processor 258 may program memory controller 256 and USB controller 260 so that read DMA controller 270 fetches payloads from memory 212 in the order requested by device 251, sends the fetched payloads to USB controller 260, and USB controller 260 sends the fetched payloads to device 251. For example, processor 258 may write to read page pointers storage 276 pointers to portions of memory 212 from which read DMA controller 270 may start fetching payloads. In addition, processor 258 may write to read/write burst size storage 277 the number of portions of memory 212 that read DMA controller 270 may fetch in one burst.

The read DMA controller 270 may access memory 212 via memory bus 278 to fetch recorded payloads during times in which write DMA controller 268 does not access memory 212. For at least this purpose, write DMA controller 268 may, for example, output an indication 284 to read DMA controller 270. According to some embodiments of the present invention, the write DMA controller 268 may assert indication 284 to, for example, a high logic level, in response to the assertion of payload valid indication 266, and may de-assert indication 284 to, for example, a low logic level, after completing writing the header to memory 212. According to some embodiments of the present invention, the read DMA controller 270 may start fetching recorded payloads from memory 212 after indication 284 is de-asserted, and may fetch from memory 212 a number of portions equal to the number stored in read/write burst size storage 277.

For example, according to some embodiments of the present invention, the number stored in read/write burst size storage 277 may be related to the number of pointers stored in read page pointers storage 276 and/or to the time available for read DMA controller 270 to fetch recorded payloads from memory 212.

Read DMA controller 270 may send processor 258 an indication over, for example, bus 262, to notify processor 258 of the end of burst.

According to some embodiments, data stored in memory may be retrieved in a forward direction, for example, according to the order in which it was collected by device 40. In other embodiments, data may be retrieved in an order other than the order in which it was collected by device 40, for example, in an order opposite the order in which it was collected, the backwards direction. According to other embodiments data may be transmitted (e.g. fetched) directly from the digital modem 254 to the USB controller 260. Thus, writing to read DMA 270 may not be necessary. According to some embodiments read DMA 270 need not be included in the receiver/recorder 230.

Device 251 may include a processor 286, at least one human interface device (HID) 288 such as, for example, a mouse or a keyboard, a memory 290, and a display controller 292 coupled to display unit 216.

According to some embodiments of the present invention, the processor 258 may be able to control the operation of USB controller 280, HID 288, memory 290 and display controller 292 through a bus 294. In addition, USB controller 280, processor 286, HID 288, memory 290 and display controller 292 may be able to exchange data, such as, for example, payloads of wireless communication frames received from receiver/recorder 230, or portions thereof, over bus 294.

According to some embodiments of the present invention, the payloads of wireless communication frames received from receiver/recorder 230 may be transferred from USB controller 280 to memory 290 in a DMA process over bus 294, or by way of processor 286.

According to some embodiments of the present invention, the images may be extracted from payloads stored in memory 290 and may be transferred to display unit 216 by way of display controller 292 to be displayed, and/or may be analyzed by processor 286.

A non-exhaustive list of examples of processors 258 and 286 includes a central processing unit (CPU), a digital signal processor (DSP), a reduced instruction set computer (RISC), a complex instruction set computer (CISC) and the like. Moreover, processors 220, 258 and/or 286 may each be part of an application specific integrated circuit (ASIC) or may each be a part of an application specific standard product (ASSP).

A non-exhaustive list of examples of device 251 may include a original equipment manufacturer (OEM) dedicated workstation, a desktop personal computer, a server computer, a laptop computer, a personal digital assistant, a notebook computer, a hand-held computer, and the like.

Other methods of transferring data from the in-vivo device 40 to the receiver/recorder 12 or 230 to device 251 or database 19 may be used.

According to some embodiments of the present invention, the process of processor 258 activating write DMA controller 268 to independently store payload bits 26 in memory 212 may repeat itself for frames of a stream of wireless communication frames. Moreover, the order in which the payloads were received from sensing device 40 may be traceable in memory 212.

According to one embodiment of the present invention, the receiver/recorder 230 or 12 may simultaneously record information received from the sensing device 40 on a memory, such as memory 212, process the information and display the information on a display, for example, display unit 216. According to another embodiment of the present invention, the receiver/recorder 230 or 12 may simultaneously record the information received from the sensing device 40 on a memory, such as memory 212, and transfer the information from the memory to a workstation.

In one embodiment, in-vivo images collected in an in-vivo database such as database 16 or a database within receiver/recorder 230 may be processed. For example, in-vivo images may be read from an in-vivo database such as database 16 or a database within receiver/recorder 230, transferred to for example to a processor, for example within a workstation such as device 251. The images may then be processed. For example, features may be extracted or diagnoses made, e.g., blood detection, color analysis, polyp detection, etc. Location or other information may be derived based on image analysis. Image clean-up or clarification may be performed, noise reduction, and color or contrast or other parameters may be adjusted. Other or different processing may be performed.

To speed processing of an image stream, and/or to allow for concurrent viewing and image gathering, one or more processors for processing may concurrently process the images, for example, using concurrently operating processors, hardware or software modules, or software processes. For example, images may be fetched from storage (e.g., an in-vivo database such as database 16 or a database within receiver/recorder 230) by different processes or processors and concurrently processed. Image may be random-access, e.g., non-consecutive images from disparate portions of the database may be fetched one after the other. In other embodiments, images may be fetched concurrently.

Figure 3:
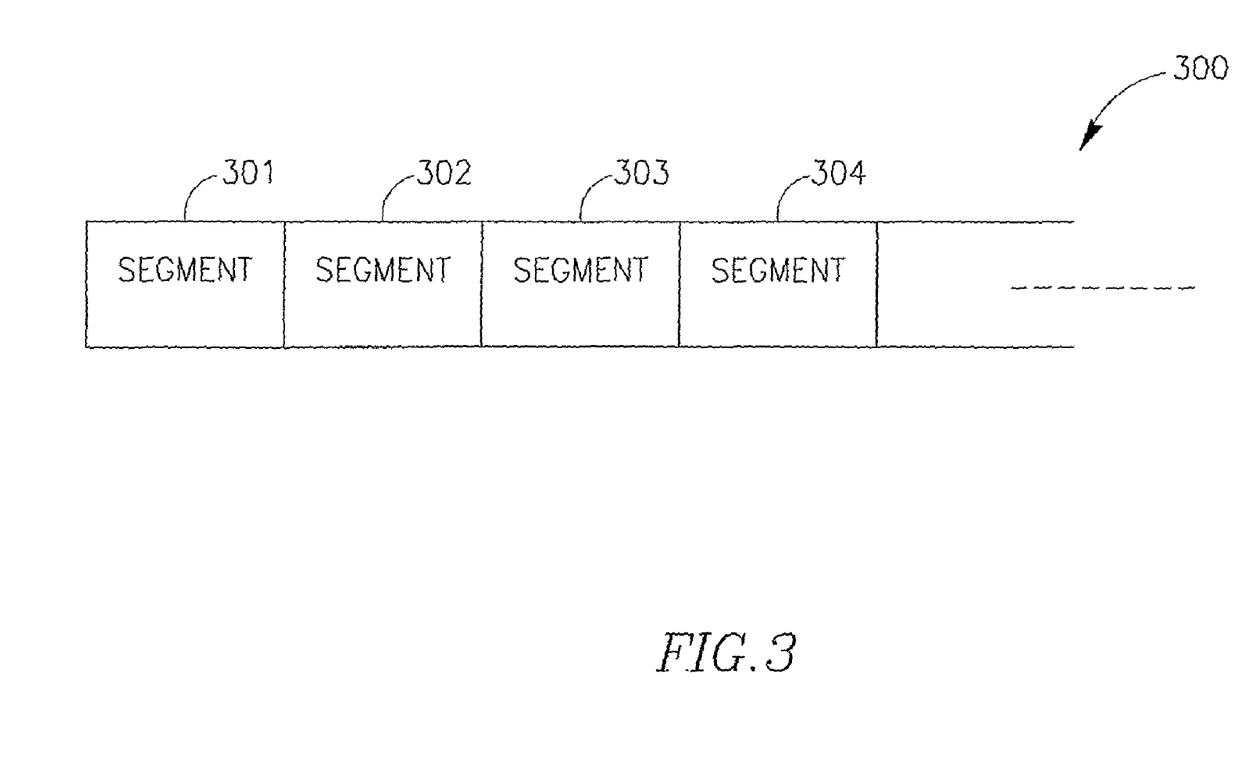
FIG. 3 is a schematic illustration of a portion of an image stream and segmentations thereof, in accordance with some embodiments of the present invention.

Reference is made to FIG. 3, which schematically illustrates a portion of an image stream 300 and segmentations thereof, in accordance with some embodiments of the present invention.

According to one embodiment of the present invention, a processor, for example, processors 220, 258, or 286 may create a plurality of segments 301, 302, 303, and 304 from at least a portion of image stream 300, for example, by marking or indicating such segmentation on image stream 300.

In one embodiment, the overall image stream may include, for example, approximately 50,000 images, and may be partitioned into segments 301, 302, 303, and/or 304, for example, portions, sections, or slices, of image stream 300. In some embodiments, segments 301, 302, 303, and 304 may include at least a plurality of contiguous (e.g., in series) images or image frames. The segments are generally fixed and may be substantially uniform in size (e.g., 2,000 images) in one embodiment, but in other embodiments need not be. The size of a segment may be determined by any form of measurement, for example, a number of image frames, a number of bytes or bits, a time length for displaying, collecting, processing, transferring the segment, etc. As is well known in the art, other forms of measurement may be used. In other embodiments, segments 301, 302, 303, and 304 may be created according to the anatomical structures being imaged. After some analysis, unit 251 may recognize the areas of the GI tract being imaged, for example, the esophagus, the stomach, etc., and may partition image stream 300 accordingly, thus creating an esophagus segment of image stream 300, a stomach segment of image stream 300, etc. Thus, segments 301, 302, 303, and 304 may each include images of substantially different anatomical regions. In another embodiment, segments 301, 302, 303, and 304 may be created to sufficiently allow for real-time viewing. For example, segments 301, 302, 303, and 304 may be created to be a size that may allow for images to be processed and displayed relatively quickly.

In one embodiment, segments 301, 302, 303, and 304 may be concurrently transferred or downloaded. In one embodiment, segments 301, 302, 303, and 304 may be transferred from device 240 to receiver/recorder 230, or from receiver/recorder 230 to device 251.

In another embodiment, segments 301, 302, 303, and 304 may be concurrently processed, for example, in processors 220, 258, and/or 286. Processors 220, 258, and/or 286 for concurrently processing may include a plurality of processors, for processing each of segments 301, 302, 303, and 304 with a different one of the plurality of processors 220, 258, and/or 286. In one embodiment, segments 301, 302, 303, and 304 may be concurrently processed, whether or not those segments 301, 302, 303, and 304 are concurrently transferred, or whether or not these segments are contiguous, one to another.

According to embodiments of the invention, concurrently executing operations, for example, transferring, or downloading, or processing the plurality of segments 301, 302, 303, and/or 304, may include executing the operations for each of the plurality of segments either in parallel, or substantially simultaneously, or at about the same time, or during overlapping time intervals. In one embodiment, segments 301, 302, 303, and 304 may be concurrently processed, depending on resources. For example, some of the segments may be substantially concurrently processed while others may wait for processing; when a process or processor completes one segment it may access another segment or group of segments for processing, depending on criteria established for which segments are to be processed next.

In some embodiments, segments 301, 302, 303, and 304 may or may not be consecutive in image stream 300. For example, an ordering for transferring, processing, or viewing segments 301, 302, 303, and 304 may be determined, for example, by unit 251. For example, priority for transferring, processing, and viewing may be given to segments determined to image in-vivo structures likely to have a pathology or bleeding. Such segments may be created and flagged for immediate transferring, processing, and/or viewing. According to one embodiment, unit 251 may conduct a preliminary analysis, either automatically or at the user's request, of each of segments 301, 302, 303, and 304, to determine such ordering. In one embodiment, a "middle" section, or a section likely, because of its position within a data stream, to be of interest, may be processed first and then viewed by a clinician, while other sections are concurrently being processed. For example, segments 301, 302, 303, and 304, created, for example, in a middle of image stream 300, starting at for example frame 20,000, may be concurrently processed with other portions of image stream 300, for example, starting at for example, frame number 1, the beginning of image stream 300.

A master process or processor may perform image fetching from an image database, based on requests from slave processes or processors; may control and assign tasks such as processing of sections to slave processes or processors; may pass completed slices to a viewing process (e.g., on a workstation) before overall processing is completed; and may assemble the processed slices or sections into an overall video stream at the end of processing.

A master process may for example run on device 251 or processor 14 and may communicate with a receiver/recorder such as receiver/recorder 230 to fetch images. Slave processes may for example run on, for example, device 251 or processor 14. Data retrieved from the receiver/recorder is typically "raw" data and may require further image processing as is known to those skilled in the art before being viewed by a health processional.

A master process or processor may fetch images from an image database in a non-sequential manner. For example, if process A processes images 1-5,000, process B processes images 5,001-10,000, and process C processes images 10,001-15,000, process A may request image 5, process B may request image 5010, and process C may request image 10,025. Other methods of fetching images may be used.

In one embodiment, a master process and slave processes may be software processes running on one Workstation or computer, such as a personal computer with multiprocessing capability or more than one processor (e.g., a multicore or dual core processor). In one embodiment, a master process and slave processes may be processes running on more than one processor, on the same or different workstation or computer. Master and slave processes may alternatively run on disparate computer systems.

Figure 4:
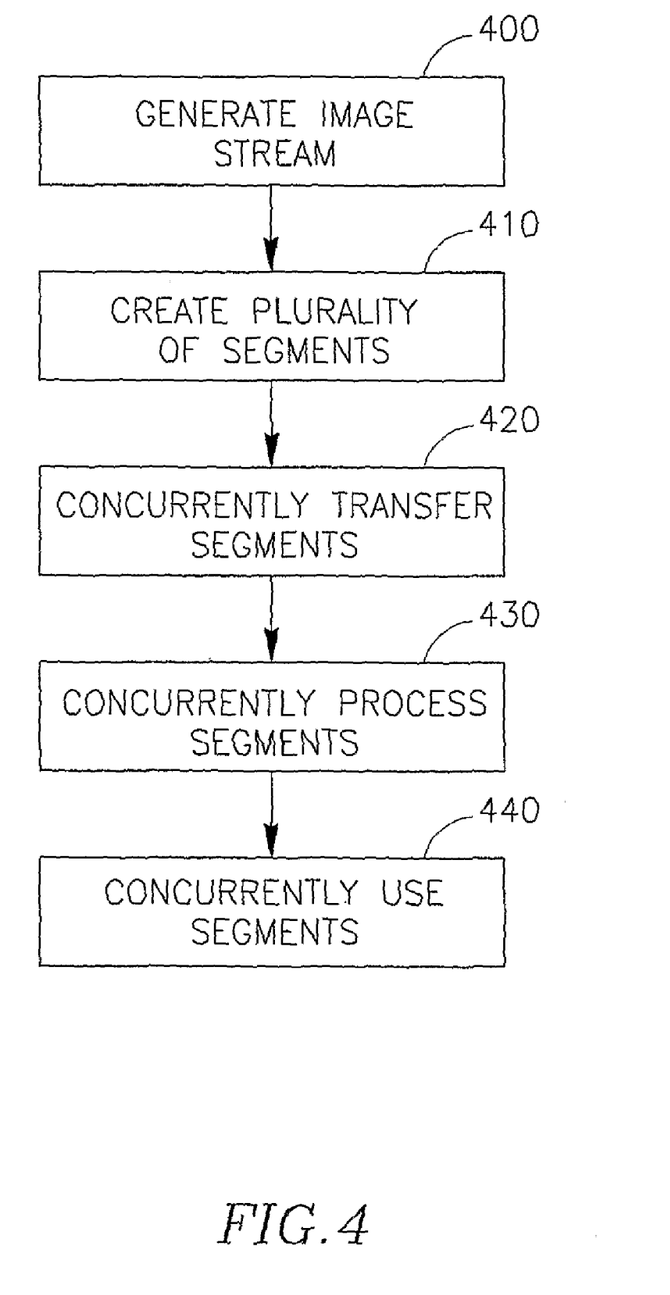
FIG. 4 is a flowchart of a method for concurrently operating on a plurality of segments of an image stream, in accordance with some embodiments of the present invention.

Reference is made to FIG. 4, which is a flowchart of a method for concurrently operating on a plurality of segments of an image stream, in accordance with some embodiments of the present invention.

In operation 400, an in-vivo sensing device may generate an image stream. For example, a swallowable capsule may capture images as the device moves through a patient's GI tract. The images may be combined or attached, for example, consecutively, to form an image stream or moving images.

In operation 410, an in-vivo sensing device may create a plurality of segments from at least a portion of the image stream. A portion of the image stream may be segmented, for example, by rearranging, separating, marking or tagging the image stream to indicate the separation of segments.

In operation 420, a processor may concurrently transfer the segments of the image stream, for example, created in operation 410. In one embodiment, the processor may include a plurality of processors, where each of the plurality of processor concurrently transfers a different one of the plurality of segments. In various embodiments, the plurality of segments may be concurrently transferred from the in-vivo sensing device to a receiver/recorder, from the receiver/recorder to a workstation, or from the in-vivo sensing device to the workstation.

In operation 430, a processor may concurrently process the segments of the image stream, for example, created in operation 410. In one embodiment, the processor may include a plurality of processors, where each of the plurality of processor concurrently processes a different one of the plurality of segments. Processors may be located in the in-vivo sensing device, the receiver/recorder, and/or the workstation. In one embodiment, the segments may be concurrently processed, whether or not those segments are concurrently transferred.

In operation 440, an in-vivo sensing system may concurrently store, process, display or use segments of the image stream transferred in operation 420 and/or processed in operation 430. Each of the plurality of segments may be stored, processed, displayed or used separately or in combination.

Other operations or series of operations may be used.

The embodiments of in-vivo image capture devices and methods described above may be used with such a system and method, but other embodiments of in-vivo image capture devices and methods may be used.

It will be appreciated by persons skilled in the art that the present invention is not limited to what has been particularly shown and described hereinabove. Rather the scope of the present invention is defined only by the claims, which follow:

What is claimed is:

1. A method for processing of an image stream gathered by an in-vivo sensing device, the image stream comprising a plurality of images of a gastrointestinal tract, the method comprising:
partitioning, by a processor at least a portion of the image stream into a plurality of segments, each segment including a plurality of images;
conducting a preliminary analysis to determine segments of interest which are likely to include an image of a pathological structure or bleeding;
determining a priority order of processing said plurality of segments, wherein at least one segment of interest is processed first;
processing said plurality of segments by a processor, according to the determined priority order of processing; and
displaying said processed segments.

2. The method of claim 1, wherein said plurality of segments comprise at least a plurality of images.

3. The method of claim 1, wherein said plurality of segments are substantially uniform in size.

4. The method of claim 1, wherein partitioning comprises partitioning at least a portion of the image stream according to anatomical structures being imaged.

5. The method of claim 4, wherein each of said plurality of segments comprises images of a different anatomical region.

6. The method of claim 1, wherein said plurality of segments are non-consecutive in the image stream.

7. The method of claim 1, further comprising determining which of said plurality of segments are likely to include an image of bleeding or a pathology.

8. The method of claim 1, further comprising transferring said plurality of segments to a display.

9. The method of claim 8, further comprising determining which of said segments to concurrently transfer.

10. The method of claim 1, further comprising concurrently fetching recorded data from storage.

11. A system for expediting processing of a raw image stream gathered by an in-vivo sensing device, the image stream comprising a plurality of images of a gastrointestinal tract, the system comprising:
a plurality of processors configured to:
partition at least a portion of the image stream into a plurality of segments, each segment including a plurality of images from the image stream;
conduct a preliminary analysis to determine segments of interest which are likely to include an image of a pathological structure or bleeding;
determine a priority order of processing said plurality of segments, wherein at least one segment of interest is processed first;
process said segments according to the determined priority order of processing; and
produce a combined image stream from the processed segments; and
a display to display the combined image stream.

12. The system of claim 11, wherein each of said segments that is processed is processed by a different one of said plurality of processors.

13. The system of claim 11, wherein said segments are non-consecutive in the image stream.

14. The system of claim 11, wherein said plurality of processors determine which of said segments to process.

15. The system of claim 11, wherein said plurality of processors concurrently transfer said segments.

16. The system of claim 11, wherein said processors are components of a receiver, a workstation or an in-vivo sensing device.

17. The system of claim 11, further comprising an external receiver, wherein the in vivo sensing device comprises a transmitter to wirelessly transmit the image stream to the external receiver.

18. The method of claim 1, wherein processing said segments comprises analyzing one or more of the plurality of images in said segments.

19. The method of claim 1, wherein processing said segments comprises at least one operation selected from the group consisting of: feature detection, feature extraction, making diagnoses, deriving location, image clean-up or clarification, noise reduction, adjusting color, adjusting contrast, and determining a size of the segments.

20. The method of claim 1, wherein processing said segments comprises processing raw image stream data.

21. The method of claim 1, comprising displaying the at least one segment of interest is review by a clinician, while other segments are being processed.

22. The system of claim 11, wherein the at least one segment of interest is displayed for review by a clinician, while other segments are being processed.

* * * * *